United States Patent [19]

McGirr

[11] Patent Number: 4,807,626
[45] Date of Patent: Feb. 28, 1989

[54] STONE EXTRACTOR AND METHOD

[76] Inventor: Douglas B. McGirr, 5362 Feather River Dr., Stockton, Calif. 95207

[21] Appl. No.: 814,905

[22] Filed: Dec. 30, 1985

Related U.S. Application Data

[63] Continuation-in-part of Ser. No. 701,417, Feb. 14, 1985, abandoned.

[51] Int. Cl.[4] .............................................. A61B 17/00
[52] U.S. Cl. ..................... 128/328; 128/345; 128/658; 128/772; 604/95; 604/107; 604/281
[58] Field of Search ............... 128/328, 345, 356, 343, 128/303 R, 348.1, 658, 772, 656, 657; 604/104–109, 49–53, 281, 284, 95, 282, 164–170

[56] References Cited

U.S. PATENT DOCUMENTS

| 1,677,671 | 7/1928 | Councill | 128/328 |
| 2,227,727 | 1/1941 | Leggiadro | 128/319 |
| 2,556,783 | 6/1951 | Wallace | 604/105 |
| 3,008,467 | 11/1961 | Morris | 128/328 |
| 3,074,408 | 1/1963 | Chester | 128/328 |
| 3,119,392 | 1/1964 | Zeiss | 128/348.1 |
| 3,334,630 | 8/1967 | Kramer | 128/328 |
| 3,413,976 | 12/1968 | Roze | 128/328 |
| 3,605,725 | 9/1971 | Bertov | 604/95 |
| 4,020,829 | 5/1977 | Willson et al. | 128/772 |
| 4,033,331 | 7/1977 | Guss et al. | 604/281 |
| 4,046,149 | 9/1977 | Komiya | 128/328 |
| 4,046,150 | 9/1977 | Schwartz et al. | 128/328 |
| 4,142,528 | 3/1979 | Whelan, Jr. et al. | 604/284 |
| 4,154,242 | 5/1979 | Termanini | 604/105 |
| 4,279,252 | 7/1981 | Martin | 128/658 |
| 4,590,938 | 5/1986 | Segura et al. | 128/328 |
| 4,610,662 | 9/1986 | Weikl et al. | 128/328 |
| 4,611,594 | 9/1986 | Grayhouk et al. | 128/328 |
| 4,616,652 | 10/1986 | Simpson | 128/772 |
| 4,625,726 | 12/1986 | Duthoy | 128/328 |

OTHER PUBLICATIONS

*Current Problems in Surgery*, Vol. XVI, No. 3, Mar. 1979 Yearbook Publ. Chicago—Figure 16 (1–6), p. 41.

Primary Examiner—C. Fred Rosenbaum
Assistant Examiner—Mario Costantino
Attorney, Agent, or Firm—Flehr, Hohbach, Test, Albritton & Herbert

[57] ABSTRACT

Extractor and method for removing stones or other foreign objects from the biliary and urinary systems or from other portions of the body. The extractor includes a self-closing basket at the distal end of a catheter, with a flexible control line for opening the basket from the proximal end of the catheter. Being self-closing, the basket closes automatically about an object captured within the basket when the control line is relaxed. The extractor can be placed in the body with the aid of a guide wire, and fluids can be injected into and removed from the body through the extractor.

14 Claims, 6 Drawing Sheets

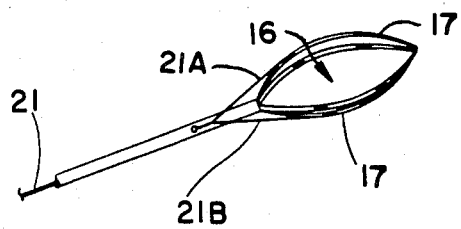
FIG. 8.
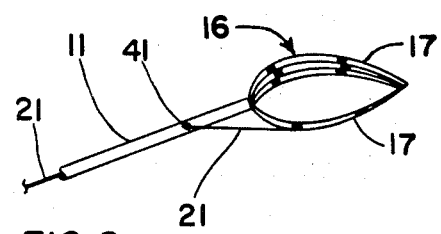
FIG. 9.
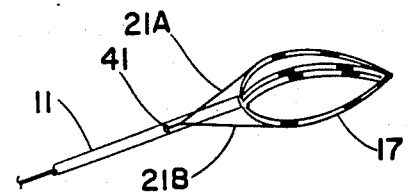
FIG. 10.
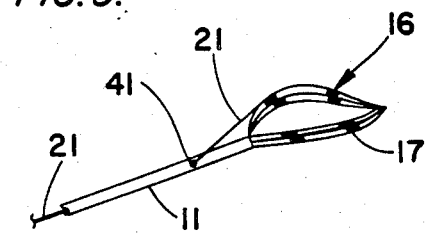
FIG. 11.
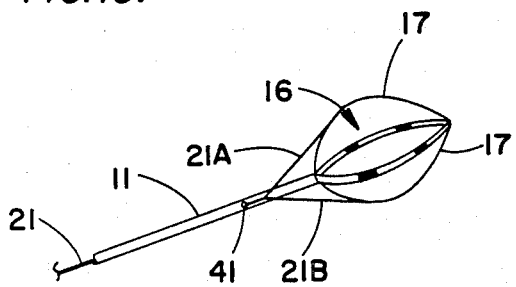
FIG. 12.
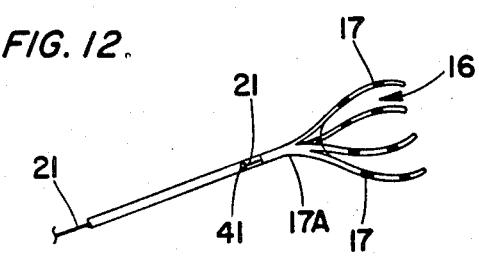
FIG. 14.
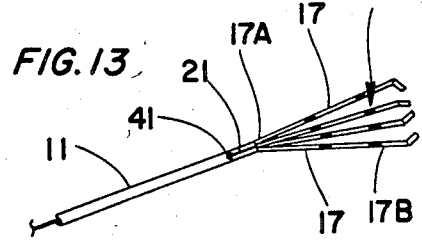
FIG. 15.
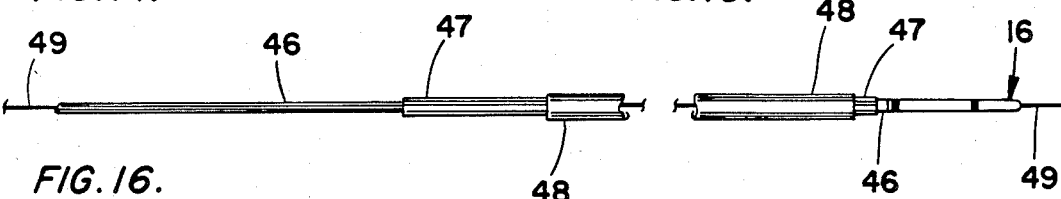
FIG. 16.
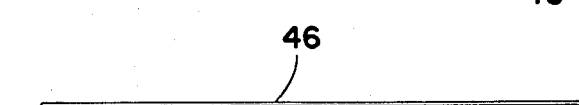
FIG. 17.
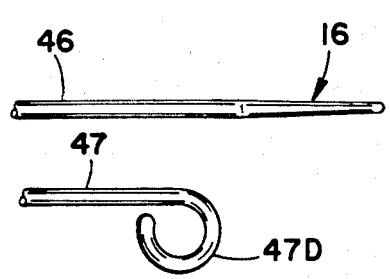
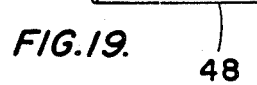
FIG. 18.
FIG. 19.

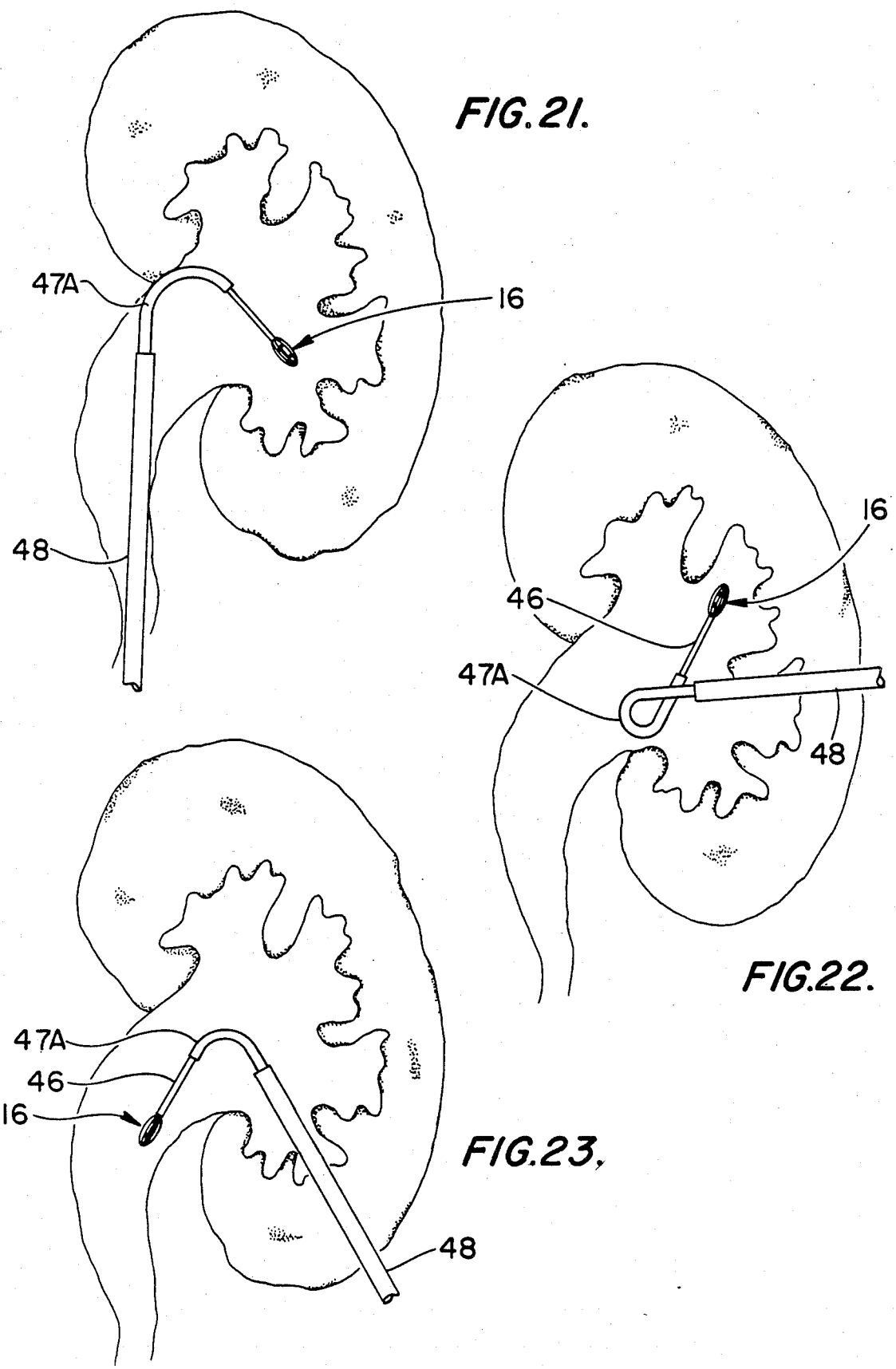

STONE EXTRACTOR AND METHOD

This is a continuation-in-part of Ser. No. 701,417, filed Feb. 14, 1985 now abandoned.

This invention pertains generally to medical instruments, and more particularly to an extractor and method for removing stones or other foreign objects from the biliary and urinary systems or from other parts of the body.

Heretofore, extractors have been provided for removing stones from the biliary and urinary systems. Most of these devices have curved wires forming a basket or cage with a sheath which can be retracted or advanced relative to the wires to open or close the basket. Examples of such extractors are found in U.S. Pat. Nos. 2,943,626, 3,472,230, 4,046,149, 4,046,150, 4,203,429, 4,299,225 and 4,347,846, German Patent No. 2,428,319 and French Patent No. 2,454,293. These devices have certain limitations and disadvantages. The baskets open a fixed amount, and the degree of closure is dependent upon the operator. It is difficult to close the basket the correct amount to grasp small stones as well as to maintain the correct degree of pressure on the stone for removal. The wires which form the baskets are relatively thin, and there is a danger they may cut delicate tissues. This limits the portions of the body in which these extractors can be safely used. The wire baskets and other extractors heretofore provided are relatively difficult to position and control. They generally cannot be placed with the aid of a guide wire, and they are difficult to observe fluoroscopically. In addition, it is often very difficult to identify the capture of a stone in the basket prior to removal of the entire device from the patient's body.

It is in general an object of the invention to provide a new and improved extractor and method for removing stones and other foreign objects from the body.

Another object of the invention is to provide an extractor and method of the above character in which the basket is self-closing and automatically grips stones of any size with the correct pressure for holding and removing the stones.

Another object of the invention is to provide an extractor and method of the above character which can be employed in parts of the body where extractors heretofore provided cannot be utilized.

Another object of the invention is to provide an extractor and method of the above character in which the basket is relatively easy to position and control and the capture of a stone can be observed fluoroscopically.

These and other objects are achieved in accordance with the invention by providing an extractor having a self-closing basket at the distal end of an elongated tubular member or catheter. A flexible control line extends between the basket and the proximal end of the tubular member for opening the basket to capture a stone when pulled. The basket returns by itself to its closed position to hold the stone when the pull on the line is relaxed. The basket comprises a plurality of normally straight flexible strips arranged circumferentially about the axis of the tubular member. The line is connected to the distal ends of the strips, and pulling the line flexes the strips to open the basket. A passageway extends axially through the tubular member and the basket, and the extractor can be inserted into the body over a guide wire which passes through this passageway. When the extractor is in place, fluids can be introduced into and removed from the body through the passageway.

In one embodiment, the extractor is inserted into the body and placed in a desired position through a guiding catheter having a distal end portion formed to a predetermined curvature. A relatively rigid steering element is advanced and retracted relative to the guiding catheter to alter the curvature of the distal end portion with the distal end portion tending to return to the predetermined curvature when the relatively rigid steering element is removed.

FIGS. 8-15 are fragmentary perspective views of additional embodiments of an extractor according to the invention.

FIG. 16 is an elevational view of an embodiment of a steerable extractor assembly according to the invention.

FIGS. 17-19 are elevational views of the components of the extractor assembly of FIG. 16.

FIGS. 21-23 illustrate the use of the extractor assembly of FIG. 16 in removing the stones from different portions of the kidney.

Figure 1:
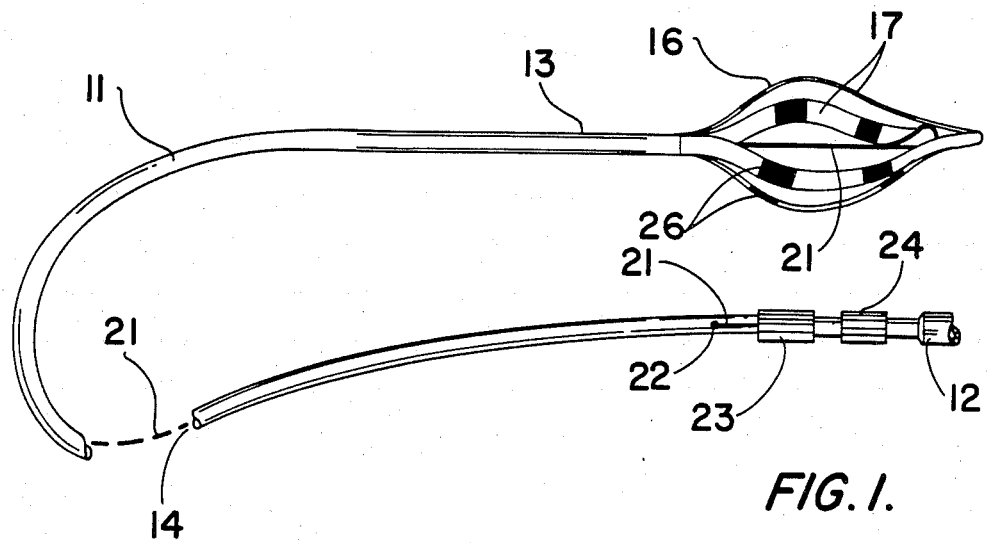
FIG. 1 is a perspective view of one embodiment of an extractor according to the invention.
Figure 2:
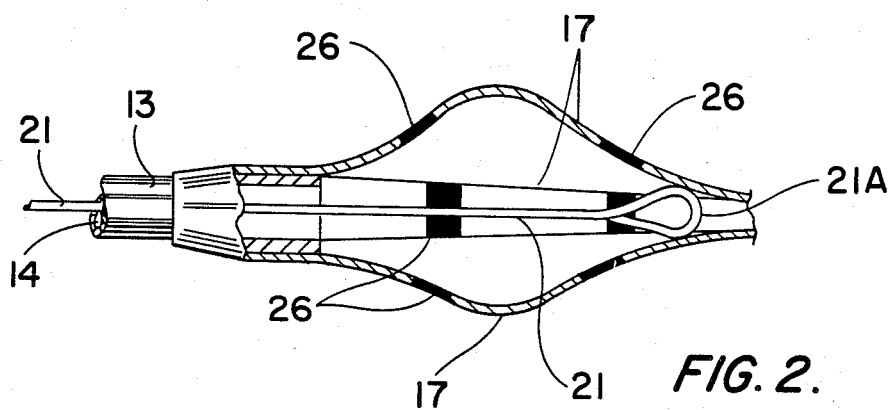
FIG. 2 is an enlarged fragmentary cross-sectional view of the embodiment of FIG. 1.

As illustrated in FIGS. 1-3 the extractor includes an elongated flexible tubular member or catheter 11 having a proximal end 12, a distal end 13 and an axially extending passageway 14. The catheter is fabricated of a stiff yet pliable material such as nylon or a polyester. A hub 15 is provided at the proximal end of the catheter for attachment to other devices such as a syringe.

Figure 3A:
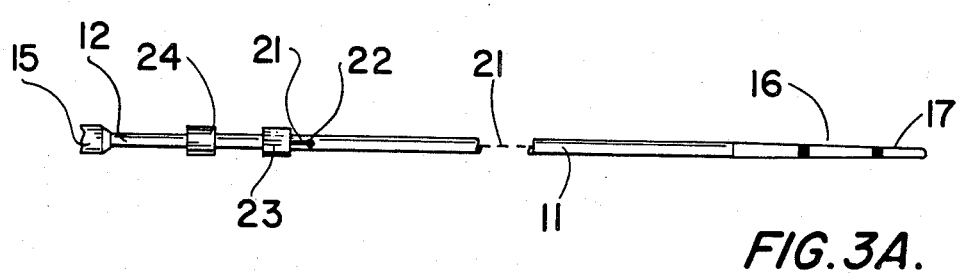
FIGS. 3A and 3B are elevational views of the extractor of FIG. 1 showing the basket in its closed and open positions, respectively.
Figure 3B:
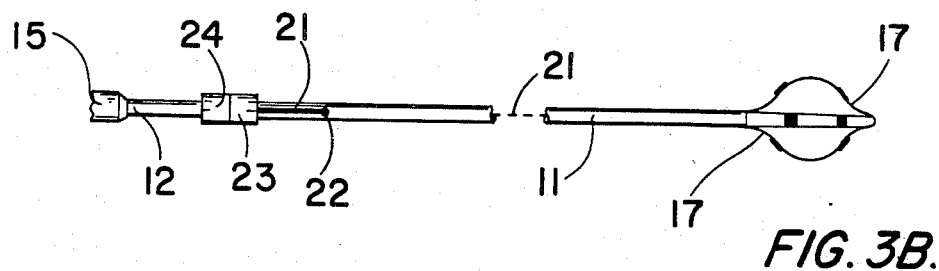

A self-closing stone basket 16 is provided at the distal end of the catheter. This basket comprises a plurality of flexible strips 17 arranged circumferentially about the axis of the catheter. In the embodiment illustrated, four such strips are provided, and they are spaced in quadrature about the axis. It will be understood, however, that any other suitable number of strips can be employed. When the basket is in its closed position, the strips are straight, and they extend in an axial direction from the distal end of the catheter, as illustrated in FIG. 3A. When the basket is in its open position, the strips bow in an outward direction, and they are spread circumferentially apart, as illustrated in FIGS. 1, 2 and 3B. The strips are fabricated of a flexible material which tends to return to its original shape when deflected therefrom. In this embodiment, the strips are normally straight, and the basket tends to return to the closed position.

In one presently preferred embodiment, basket 16 is formed by cutting longitudinally extending slits in a small rectangular sheet of plastic material, rolling the sheet into a cylindrical configuration, and bonding one end of the basket thus formed to the distal end of the catheter. Alternatively, with a catheter fabricated of a suitable material, the basket can be formed by cutting longitudinally extending slits in the distal end of the catheter itself. The distal portion of the catheter may be narrowed such that the basket diameter is equal to or less than the diameter of the body of the catheter. The outer connection of the basket and catheter is smooth such that it will slide easily past delicate tissues.

Flexible strips 17 have a relatively thin generally rectangular cross-section, and they are fabricated of a relatively soft material which will not cut or otherwise injure the delicate tissues of the body. This enables the extractor to be used safely throughout the biliary and renal tracts, whereas conventional wire baskets generally cannot be used throughout the entire ureter for fear of cutting the iliac artery or veins adjacent to the ureter. As best illustrated in FIGS. 2 and 3, the strips are tapered, being somewhat wider at their proximal ends than at their distal ends. This gives the front portion of the extractor a tapered profile which makes it easier to maneuver past stones in relatively narrow channels. Stones often lodge adjacent to the mid portion of the basket which is optimal for capture.

A flexible control line 21 extends between the proximal end of the catheter and the basket to provide means for opening the basket. The control line extends through the passageway of the catheter, and its distal end is formed into a loop 21a which is connected to opposite sides of the basket at the distal end thereof. The proximal end of the line passes through an opening 22 in the side wall of the catheter and is connected to a control ring or sleeve 23 which is slidably mounted on the outside of the proximal end of the catheter. Another ring or sleeve 24 is affixed to the catheter and serves as a stop which limits the movement of control ring 23. Control line 21 can be fabricated of any suitable material, and in one presently preferred embodiment, it is a monofilament nylon line. The monofilament line is desirable because it has a relatively small diameter and does not interfere appreciably with the passage of fluids or a guide wire through the passageway in the catheter.

Fluoroscopically visible markers 26 are provided on strips 17. Two such markers are provided for each strip, and they are spaced approximately equidistant from each other and from the ends of the basket. When the basket is moved from its closed position to its open position, the markers separate radially, permitting the state as well as the position of the basket to be observed. The markers can be any suitable radiopaque material such as metal of relatively high density. The markers should be placed such that the outer portion of the basket remains smooth.

Basket 16 is open at its distal end, and passageway 14 extends all the way through the catheter and the basket. This enables the extractor to be placed in the body on a guide wire which passes through the passageway, and it also enables fluids to be injected into and removed from the body through the passageway.

Operation and use of the extractor, and therein the method of the invention, are as follows. The extractor is inserted into the portion of the body where the stone or other object to be removed is located with the basket in its closed position. The insertion can be made over a guide wire, or the catheter can be shaped with a curvature to facilitate insertion into areas such as the biliary system or the renal pelvis. Alternatively, the extractor can be introduced through a steerable catheter or an endoscope, if desired. The positioning of the basket relative to the stone can be observed fluoroscopically. When the basket is positioned laterally adjacent to the stone, the basket is opened by sliding ring 23 toward stop 24. This exerts an axial pull on control line 21 which draws the distal end of the basket toward the proximal end, flexing strips 17 outwardly to open the basket. The basket is then rotated gently to capture the stone. Once the stone is in the basket, the control ring is released and the basket is allowed to close automatically about the stone. Thereafter, the basket grips the stone as it is withdrawn from the body. Captured calcified stones are seen between the fluoroscopic markers. Non-calcified stones are identified with the injection of contrast material through the catheter directly into the basket. The smooth flat pliable strips of the basket will not cut or otherwise injure the body tissues, and they protect the soft tissues from the rough edges of the stone. The basket material may be transparent such that stones are easily seen when the device is removed from the body.

Figure 4:
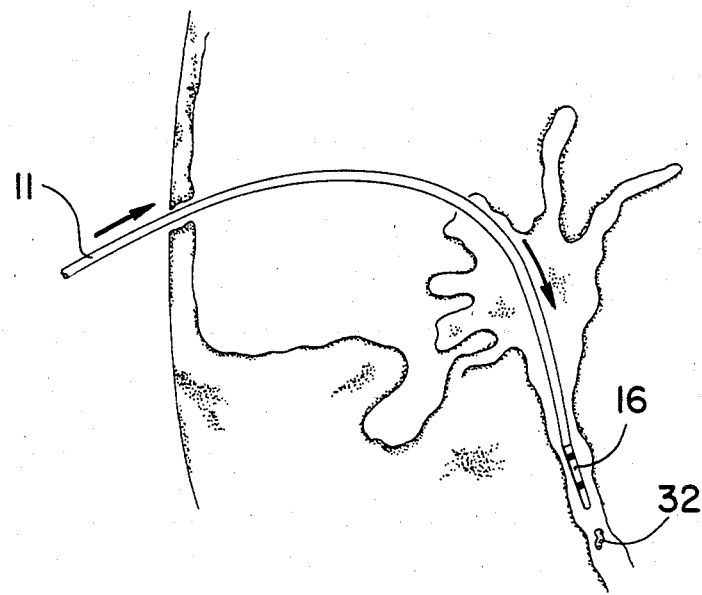
FIGS. 4-6 illustrate the use of the extractor of FIG. 1 in the percutaneous removal of stones from the liver and kidney.
Figure 5:
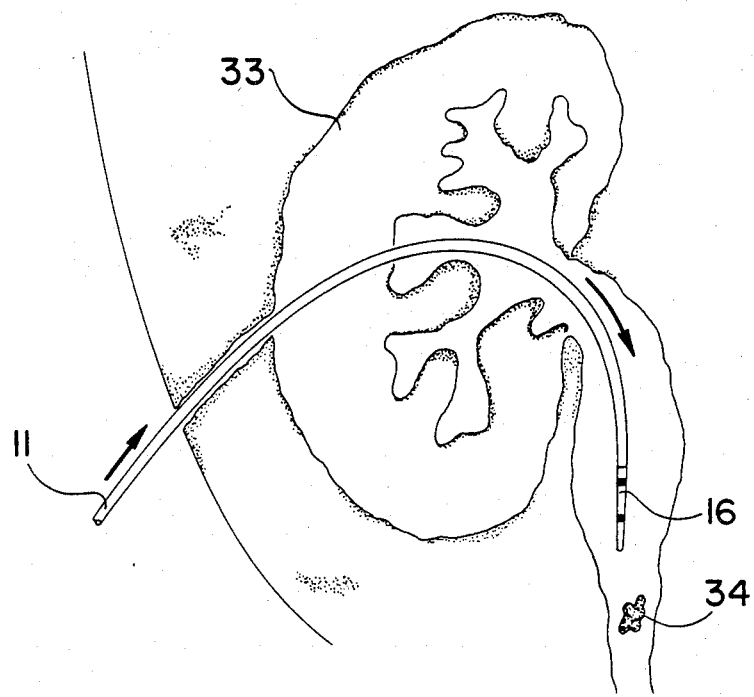
Figure 6:
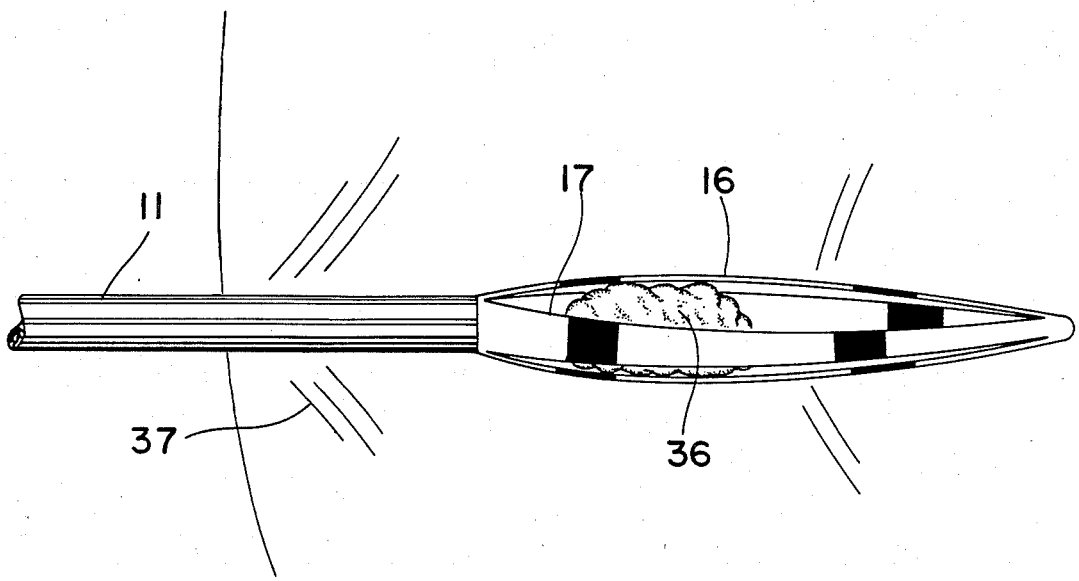

With the basket in its closed position, the outer diameter of the basket is relatively small. This small diameter and the ability of the extractor to follow standard guide wires make the extractor particularly suitable for percutaneous use through vascular organs such as the liver and kidney. FIG. 4 illustrates a percutaneous biliary approach in which the extractor is inserted through the liver 31 to remove a stone 32. FIG. 5 illustrates a percutaneous renal approach in which the extractor is inserted through the kidney 33 to remove a stone 34. The shape of the basket allows the extractor to be pulled through narrow tracts less painfully and more safely. The basket remains closed to a minimum diameter with the strips of the basket protecting the adjacent soft tissues from the rough edges of the stone. This allows safer, faster and less painful removal of calculi percutaneously. FIG. 6 illustrates the basket removing a stone 36 through a relatively small opening in the outer body tissue or skin 37.

Figure 7:
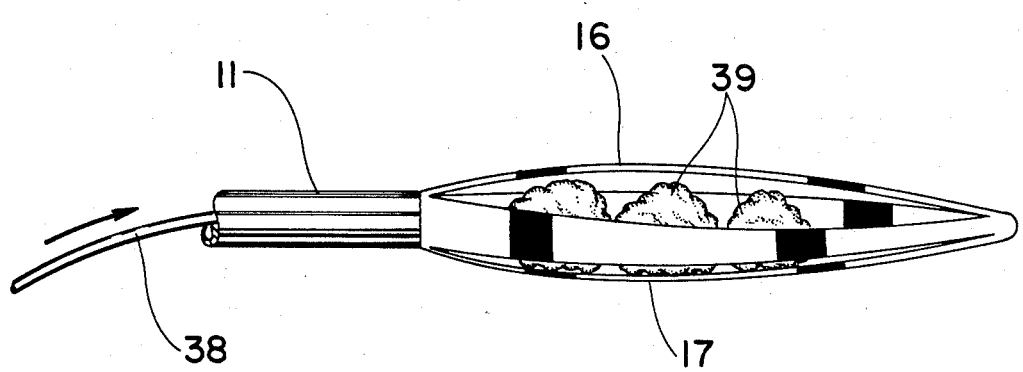
FIG. 7 is a fragmentary view illustrating the use of the extractor of FIG. 1 in breaking up a stone prior to removal from the body.

As illustrated in FIG. 7, a relatively stiff guide wire 38 can be inserted into the basket through passageway 14 to break a relatively large stone into smaller fragments 39 for easier removal. The self-closing basket automatically closes to the proper diameter to grip whatever is in it, and the smaller fragments are thus held securely by the basket for removal from the body. Suction can be applied to the basket through the catheter to assist in the capture of small stones.

Stones may be held by the basket during dissolution or reduction in size with drugs such as monooctanoin. The drug is delivered through the catheter and into the basket for optimal direct contact. Large stones may be reduced in size and later removed through small tracts.

The embodiments illustrated in FIGS. 8–15 are generally similar to the embodiment of FIG. 1, and the like reference numerals designate corresponding elements in the various embodiments. The embodiments differ primarily in the manner in which the control line is connected to the basket and the manner in which the basket opens and closes about the stone or other object to be removed. In each of these embodiments, the basket is fabricated of flexible material such as a thermoplastic which tends to return to its original shape when deflected therefrom, and the basket is self-closing as in the embodiment of FIG. 1.

In the embodiment of FIG. 8, the basket 16 has two pairs of flexible strips 17 positioned diagonally of each other on opposite sides of the basket. For approximately the first one-quarter ($\frac{1}{4}$) of their length, the strips in each pair may be joined together as a single strip or overlap one another such that they tend to flex outward as a pair. Control line 21 passes through an opening 41 in the side wall of catheter 11 toward the distal end thereof. The line splits into two strands of 21a and 21b which are connected to strips 17 slightly before the midpoints of the strips. An axial pull on the control line draws the opposing pairs of strips apart, thereby opening the basket in a loop-like configuration as illustrated in FIG. 8, with two strips on each side of the loop. A gentle rotation of the catheter with the basket in its open position helps to position the loop around the stone or object to be removed. When the pull on the control line is relaxed, the basket closes about the stone, and the stone is held firmly at the center of the basket between the four strips.

In the embodiment of FIG. 9, control line 21 passes through an opening 41 in the side wall of catheter 11 and is connected to one of the four strips 17 of the basket 16. The control line is connected to the strip near the midpoint of the strip, and an axial pull on the control line causes the strip to flex in an outward direction away from the other three strips as illustrated in FIG. 9. The basket opens in a loop-like fashion with the pulled strip on one side of the loop and the other three strips on the other side. The strip which is pulled can be slightly longer or wider than the other three strips in order to urge those three strips to remain close together when flexing. When the basket is closed about a stone, the stone is held in a symmetrial manner between all four of the strips.

In the embodiment of FIG. 10, control line 21 again passes through an opening 41 in the side wall of catheter 11 and splits in to two strands, 21a and 21b, which are connected to adjacent basket strips 17 near the midpoints of these strips. The control line draws these two strips apart in an outward direction when pulled, opening the basket in a cup-like fashion as illustrated in FIG. 10. A stone is captured in the open basket by gently rotating the catheter, and when the basket is closed, the stone is held firmly by the four strips.

The embodiment of FIG. 11 is similar to the embodiment of FIG. 8 in that the basket strips 17 are grouped in pairs on opposite sides of the basket, with the lower or proximal portions of the strips in each pair being joined together as a single strip or overlapping one another such that they flex outward as a pair. In this embodiment, however, control line 21 is connected to only one of the two pairs of strips, and it pulls the basket open in an asymmetrical loop-like fashion, as illustrated in FIG. 11. The width of the loop opening can be increased by making the proximal portions of the unpulled strips wider or more rigid than the pulled strips. When the basket is closed about a stone, the stone is held in a symmetrical manner by all four of the strips.

In the embodiment of FIG. 12, the basket strips 17 are arranged in quadrature as in the embodiment of FIG. 1, and the control line has two strands 21a and 21b which are connected to opposing strips near their midpoints. Pulling on the control line draws the opposing strips apart in an outward direction, opening the basket in a symmetrical manner. The stone can enter the basket between any two adjacent strands, and when the basket is closed, the stone is gripped by all four of the strands. The basket may be fabricated of a material which allows some lateral deflection of the strips. This allows stones to enter the basket even though they may be slightly larger than the openings between the strips.

In the embodiments of FIGS. 13–15, the proximal portions of the strips are composed of two layers of thermoplastic material. The inner layer of the strips are bound to the catheter while the outer layer of strips are not bound to the catheter but are bound to one another. The control line 21 pulls the ring of outer strips 17a as a unit proximally. The outer layer of strips unite with their inner layer near the mid portion of the basket such that they flex open the basket when pulled.

In the embodiment of FIG. 13, the strips are arranged in quadrature such that the basket opens symmetrically. However, placing the outer layer of strips on opposing pairs would open the basket in a loop configuration similar to FIG. 8.

With the control line positioned outside the basket, as in the embodiments of FIGS. 8–13, it does not block the entrance of larger stones into the basket, as can sometimes happen when the line is inside the mid portion of the basket. With the control line outside the functional portion of the basket, as in the embodiments of FIGS. 8–13, a portion of the basket is pulled open, rather than having the entire basket flex open as in the embodiment of FIG. 1. This ensures that the strips will move in the desired outward direction when the line is pulled, yet lessens the chance of the strips deflecting inwardly in the wrong direction. In the embodiments of FIGS. 8–11, the basket opening is relatively wide, and these embodiments are particularly suitable for use in confined areas such as the ureter. The entrance to the basket is nearly as large as the overall diameter of the open basket, and this allows the basket to engage stones with a minimal degree of opening. The basket opens around the stone, and this protects the ureter or biliary system from undesired dilatation and possible injury. The embodiments of FIGS. 1, 12, and 13 are particularly well-suited for engaging stones in less confined regions such as a large bile duct or renal pelvis. The symmetrical manner in which the embodiments of FIGS. 1, 12 and 13 open allows stones to be engaged from different directions and requires less precise positioning and maneuvering of the basket to capture the stones.

The embodiments illustrated in FIGS. 14 and 15 are particularly suitable for engaging stones in blind ending areas such as the renal calyx as well as in less confined regions such as the bladder or a large renal pelvis. These embodiments differ from the other embodiments in that the distal end portions of the basket strips 17 are not connected together.

In the embodiments of FIGS. 14 and 15, the strips are arranged in quadrature about the catheter. As in the embodiment of FIG. 13, the proximal portions of the strips are composed of two layers with the proximal inner layer being bound to the catheter and the proximal outer layer forming a ring around the catheter. The pull of the control line 21 moves the outer layer proximally along the catheter such that it flexes the inner layer and basket open. The basket opens at its distal end to capture the stone. With the basket in its open position, the catheter is advanced, and the strips slide past the stone to capture it. In the embodiment of FIG. 14, the strips are formed with a gentle curvature such that the stone tends to be trapped at the center of the basket when the basket is closed. In the embodiment of FIG. 15, the basket strips are relatively straight, and the end portions 17b are folded back in an inward direction at an acute angle to form fingers which deflect and pass relatively freely over the stone as the basket is advanced. When the basket is retracted, the fingers abut against the stone and retain it from escaping through the distal end of the basket.

While the arrangement of the strips in quadrature as embodied in FIGS. 14 and 15 is ideal for capturing spherical objects such as stones, the strips may also be arranged in opposing pairs which is more suited for capturing tubular objects such as pieces of catheter.

In each of the embodiments, the precise configuration which the open basket assumes can be varied by altering the composition or configuration of the basket strips, e.g., the width, thickness, or flexibility of the strips. The configuration can also be changed by changing the point at which the control line is connected to the basket. The outer portion of the basket can be coated with a soft material to protect delicate tissues which may be contacted by the basket. Fluoroscopically visible markers similar to markers 26 can be employed in all of the embodiments, and the size and/or position of the markers can be selected to facilitate identification of the entrance to the basket. In each embodiment, the basket assumes a generally tubular configuration upon closing, and this configuration is particularly well-suited for passage along a guide wire therein. A stop such as a small bead (not shown) attached to the control line outside the distal end of the catheter can be employed to limit the amount the basket opens to protect both the basket and the patient's tissue from excessive distention.

The steerable extractor assembly illustrated in FIG. 16–19 comprises a stone extractor 46, a guiding element 47, and a steering element 48. The extractor can be an one of the embodiments disclosed above, with a self-closing stone basket 16 at the distal end of the catheter 11. Guiding element 47 comprises an elongated tubular member or catheter having its distal end portion formed to a predetermined curvature. The extractor passes through the passageway of the guiding element, and being more flexible than the guiding element, follows the path of the guiding element. Steering element 48 is more rigid than the guiding element, and it can be advanced and retracted relative to the distal end portion of the guiding element to change the curvature of that element. In the embodiment of FIGS. 16–19, the steering element is a tubular member of greater diameter and shorter length than the guiding element, and it slides telescopically over the guiding element. The guiding element is shorter than the extractor, and the basket can be advanced beyond the distal end of the guiding element.

Figure 20A:
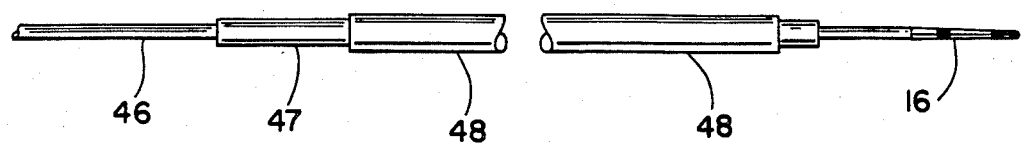
FIGS. 20A-20E are elevational views illustrating the operation of the extractor assembly of FIG. 16.
Figure 20B:
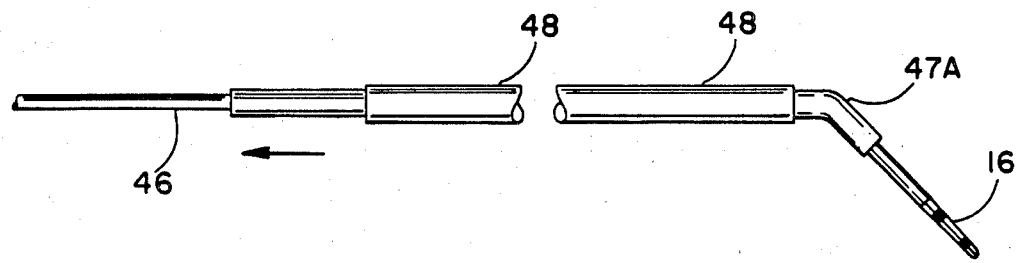
Figure 20C:
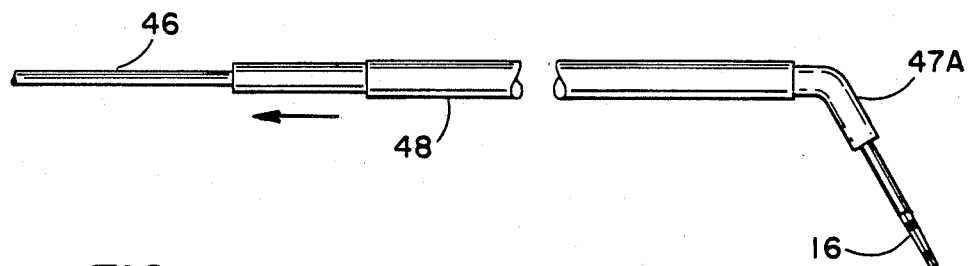
Figure 20D:
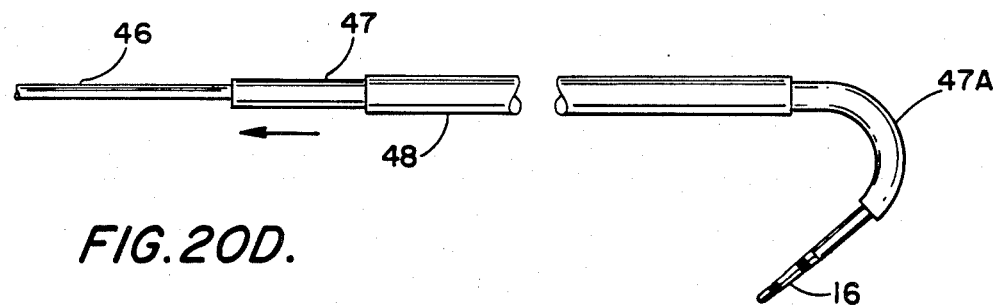
Figure 20E:
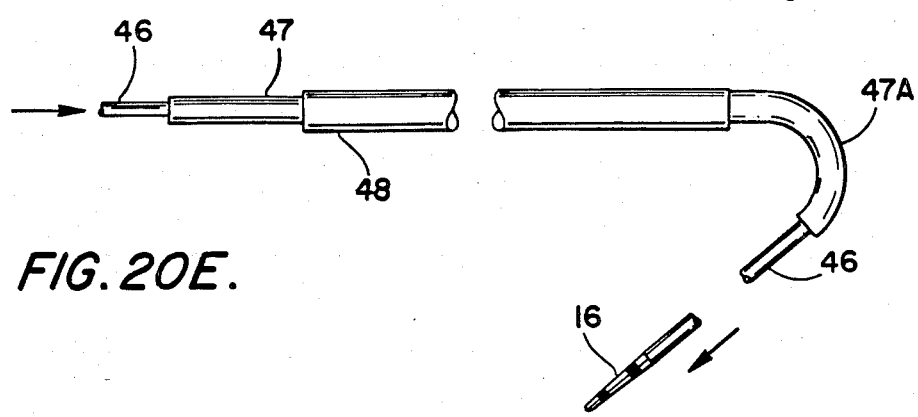

Operation and use of the steerable extractor assembly is best understood with reference to FIGS. 20A–20E. In the particular embodiment, the distal end portion 47a of the guiding element has a generally circular configuration with a curvature on the order of 360°, and steering element 48 is straight. FIG. 20A illustrates the assembly in a straight condition with extractor 46 positioned coaxially within guiding element 47 and steering element 48 in its fully advanced position. Basket 16 extends beyond the distal end of guiding element 47. As steering element 48 is progressively retracted, as illustrated in FIGS. 20B–20D, the distal end portion 47a of the guiding element assumes increasing degrees of curvature, with the extractor basket still extending beyond the distal end of element 47. When the desired curvature is achieved, the extractor can be advanced as illustrated in FIG. 20E to position the basket adjacent to the stone or object to be removed.

Guiding element 47 is fabricated of a material which gives the distal end portion of the element the ability to return to the curvature or configuration in which it is formed after numerous deflections therefrom. With a straight steering element, the distal end portion of the guiding element can be set to any desired curvature between the straight line (0°) and the curvature with which it is formed. A curvature on the order of 360° is particularly useful for removing stones from areas where an acute angulation (e.g. 20°) might otherwise be required.

The steerable extractor assembly is safer to use than conventional steerable catheters. Almost any desired curvature can be provided, and small acute angulations can be made in the biliary and renal systems without injury to tissues. The only force required to achieve the desired curvature is the intrinsic force of the catheter material returning to its original configuration, and this is substantially less force than is present in systems in which wires or cords manually flex the distal portion of a catheter. The catheter material itself can be softer and more pliable than that used in other steerable catheters since a force does not have to be transmitted through the catheter to create bending. The coaxial steering technique provides effective steering with a smaller diameter and greater length than other steering techniques.

If desired, various types of guide wires can be employed to increase the rigidity and maneuverability of the relatively small extractor catheter over longer distances. Such guide wires will also allow the catheter to be more easily visualized with a fluoroscopic instrument.

The embodiment of FIGS. 16–19 permits precise angulation of small thin long pliable catheters. As illustrated in FIG. 21, the extractor can be used through the ureter with the basket 16 directed accurately into any desired calyx from renal pelvis.

FIG. 22 illustrates the use of the steerable extractor to remove a stone from an adjacent calyx of the kidney. The steerable extractor is more flexible and can transverse narrower channels than the optical instruments themselves. With fluoroscopic guidance, the extractor can percutaneously remove small stones which are inaccessible to the nephroscope. The system can retrieve stones which were previously difficult or impossible to retrieve without creating additional percutaneous routes to the kidney.

FIG. 23 illustrates the use of the steerable extractor for removing a stone through a narrow nephrostomy tract in the lower portion of the kidney area. This system may use a relatively safe approach to the kidney since the lung which is adjacent to the upper portion of the kidney is easily avoided. This steerable system does not require that the percutaneous route used point directly to the stone. The basket may easily be directed to all regions of the kidney from a single percutaneous tract which is in a low and safer position. Also, the width of the percutaneous tract need be only wide enough to accommodate the width of the stone during removal. The larger percutaneous tracts required for optical instruments are not required.

The steering element can comprise a rigid guide wire 49 in place of or in addition to the tubular element 48 in the embodiment of FIGS. 16–19. The guide wire can pass through the inner passageway of the extractor catheter and straighten the curvature of the guiding catheter as it is extended or advanced relative to the distal end portion of that catheter. The guide wire can be either a one-piece guide wire or a guide wire having a solid rigid core which slides inside a flexible outer member. This technique of replacing element 48 with a straightening guide wire reduces the overall outer diameter the system requires.

A method of catheter exchange reduces the outer diameter of the system to a minimum such that it can be effectively used through narrow channels such as a T-tube tract to the biliary system as well as through narrow channels in optic instruments such as a gastroscope or bronchoscope.

In this method the guide wire serves as the straightening element such that element 48 is not required. The curvature of element 47 is adjusted by the guide wire allowing the system to be steered into the desired position. The diameter of element 47 is reduced such that it is the same diameter of element 46 and readily passes over the guide wire. After the system is in the desired location the guide wire is left in place. The steering catheter is removed and exchanged for the basket catheter (element 46) which has the same small diameter. The basket catheter now may be advanced over the guide wire and the basket positioned adjacent to the stone for capturing it. This catheter exchange method keeps the overall catheter diameter to a minimum. This method is practical in narrow passageway which accommodates the guide wire such as the biliary system, ureter, intravascularly and the lung. FIGS. 4 and 5 illustrate potential uses of this method percutaneously.

The coaxial system as illustrated in FIGS. 16 and 20 is more practical in areas such as the renal pelvis or bladder where guide wire guidance is less practical. FIGS. 21 through 23 demonstrate some of the uses of the complete coaxial system.

As discussed above, the extractor can be directed into the body in a number of different ways. The optimal method used depends on the location within the body as well as if optical instruments are used.

If desired, the positions of the extractor, the guiding element and the steering element can be interchanged if elements of the proper diameter are employed. For example, the extractor catheter can be positioned outside the guiding element, with a guide wire inside the guiding element for straightening the curvature of that element. Similarly, the guiding element with the curved distal end portion can be the outer element, the straightening element can be the middle element, and the extractor can be positioned inside the straightening element. The guiding element can also be formed with a double lumen, with the straightening element in one of these passageways, and the extractor in the other.

A guide wire allows the extractor to pass safely along the side of large stones rather than forcing them more distally into the ureter or biliary system. With a rigid guide wire, the extractor can even slide past impacted stones so that they can be effectively removed.

The extractor may be used in conjunction with ultrasonic and hydraulic stone crushing devices. The extractor may also be used to remove fragments of stones left following extracorporeal ultrasonic stone dissolution.

The invention has a number of important features and advantages. It overcomes the major difficulties of extractors heretofore provided. It is easily directed to a desired position with a guide wire, and the markers on the basket permit the position and the state of the basket to be monitored easily with a fluoroscope. The capture of a stone can be verified fluoroscopically before the extractor is removed from the body. The self-closing basket securely holds stones during removal, and the extractor is easy to operate and safer to use than most extractors heretofore provided. The device can be used in smaller channels and tracts than other extractors, and it can also be used percutaneously. With the invention, it is possible to remove small calculi which were previously difficult or impossible to remove.

It is apparent from the foregoing that a new and improved extractor and method for removing stones and other foreign objects from the body have been provided. While only certain presently preferred embodiments have been described in detail, as will be apparent to those familiar with the art, certain changes and modifications can be made without departing from the scope of the invention as defined by the following claims.

I claim:

1. In a method of removing a foreign object from the body with an extractor having a self-closing basket comprising a plurality of strips of a nonmetallic flexible material joined together at their proximal and distal ends at the distal end of a catheter, a passageway which extends axially through the catheter and the basket, and a flexible control line extending between the basket and the proximal end of the catheter for opening the basket when pulled, the steps of: introducing the extractor into the body along a guide wire which passes through the passageway and both ends of the basket, positioning the basket adjacent to the object, withdrawing the guide wire, exerting an axial pull on the control line to flex the strips and separate them laterally to thereby open the basket to capture the object, relaxing the pull on the line to allow the strips to straighten by themselves to close the basket about the object, and withdrawing the extractor and the object in the basket from the body.

2. The method of claim 1 including the steps of providing fluoroscopically visible markers on the basket, and observing the markers with a fluoroscope to determine the position of the basket.

3. The method of claim 1 including the step of injecting a fluid into the body through an axially extending passageway in the catheter.

4. The method of claim 1 including the step of introducing a relatively stiff wire into the basket through an axially extending passageway in the catheter, and manipulating the wire to break up the object in the basket before the object is removed from the body.

5. The method of claim 1 including the step of introducing a drug through the catheter to dissolve or reduce the size of a stone in the basket.

6. In a method of removing a foreign object from the body with an extractor comprising a catheter with a basket for capturing the object at the distal end thereof, an elongated guiding element of lasser flexibility than the extractor having a distal end portion formed with a predetermined curvature, and a relatively rigid steering element which can be advanced and retracted relative to the guiding element to change the curvature of the distal end portion of the guiding element, the steps of: introducing the guiding element and the steering element coaxially together into the body from which the object is to be removed, advancing or retracting the steering element and the guiding element relative to each other to control the curvature of the distal end portion of the guiding element and thereby steer said elements to a desired position as they are advanced into the body, removing the guiding element from the body with the steering element remaining in the desired position, introducing the extractor into the body coaxially along the steering element, and advancing the extractor basket beyond the distal end of the steering element into position for capturing the object.

7. The method of claim 6 wherein the guiding element comprises a pre-shaped reformable catheter, and the steering element comprises a relatively rigid guide wire which tends to straighten the catheter.

8. In an extractor for removing a foreign object from the body: an elongated flexible tubular member having proximal and distal ends and a longitudinally extending luminal opening, a plurality of normally straight strips of a nonmetallic flexible material extending longitudinally from the distal end of the tubular member and being connected together at their distal ends to form a normally closed basket which can be opened by flexing the strips to separate them laterally, means forming an opening at the distal end of the basket in axial alignment with the luminal opening in the tubular member whereby the extractor can be inserted into the body and advanced along a guide wire which passes freely through the luminal opening and the opening at the distal end of the basket, and a flexible control line connected to at least one of the strips forming the basket and extending to the proximal end of the tubular member for flexing the strips to open the basket when pulled, said strips tending to return to their normally straight condition to close the basket when the control line is relaxed.

9. The extractor of claim 8 wherein the strips of flexible material are fabricated of a thermoplastic material which tends to return to its original shape when deflected therefrom.

10. The extractor of claim 8 including a ring slidably mounted on the tubular member near the proximal end thereof and connected to the control line for exerting a pull on the line when moved in an axial direction on the tubular member.

11. The extractor of claim 8 including fluoroscopically visible markers on the flexible strips between the proximal and distal ends of the baskets.

12. The extractor of claim 11 wherein each of the strips has two markers spaced axially form each other and from the ends of the basket.

13. The extractor of claim 8 wherein the control line comprises a monofilament line.

14. The extractor of claim 8 wherein each of the strips forming the basket is tapered longitudinally, being wider at its proximal end than at its distal end.

* * * * *